United States Patent
Rault et al.

(10) Patent No.: US 11,045,645 B2
(45) Date of Patent: Jun. 29, 2021

(54) IMPLANTABLE LEAD FOR ELECTRICAL STIMULATION AND/OR FOR COLLECTING ELECTRICAL POTENTIALS ON AN ORGAN, INCORPORATING A PASSIVE COMPONENT FUNCTION

(71) Applicant: SORIN CRM SAS, Clamart (FR)

(72) Inventors: Maxime Rault, Paris (FR); Patrick Le Gousse, Viry Chatillon (FR)

(73) Assignee: Sorin CRM SAS, Clamart (FR)

( * ) Notice: Subject to any disclaimer, the term of this patent is extended or adjusted under 35 U.S.C. 154(b) by 226 days.

(21) Appl. No.: 16/077,348

(22) PCT Filed: Feb. 16, 2017

(86) PCT No.: PCT/EP2017/053485
§ 371 (c)(1),
(2) Date: Aug. 10, 2018

(87) PCT Pub. No.: WO2017/140768
PCT Pub. Date: Aug. 24, 2017

(65) Prior Publication Data
US 2019/0083778 A1    Mar. 21, 2019

(30) Foreign Application Priority Data
Feb. 16, 2016 (FR) ...................... 1651215

(51) Int. Cl.
*A61N 1/05* (2006.01)
*A61B 5/24* (2021.01)
(Continued)

(52) U.S. Cl.
CPC .............. *A61N 1/0556* (2013.01); *A61B 5/24* (2021.01); *A61B 5/6877* (2013.01);
(Continued)

(58) Field of Classification Search
CPC .............. A61B 5/04001; A61B 5/6877; A61N 1/0556; A61N 1/36053; H05K 1/038; H05K 3/103
(Continued)

(56) References Cited

U.S. PATENT DOCUMENTS 4,602,624 A    7/1986 Naples et al.
6,210,771 B1 *    4/2001 Post ..................... H05K 3/10
                                              428/100
(Continued)

OTHER PUBLICATIONS

Castano et al., "Smart Fabric Sensors and E-Textile Technologies: A Review", Smart Materials and Structures, IOP Publishing LTD, Bristol, GB, vol. 23, No. 5, Apr. 1, 2014. 28 pages.
(Continued)

*Primary Examiner* — Jonathan T Kuo
*Assistant Examiner* — Vynn V Huh
(74) *Attorney, Agent, or Firm* — Foley & Lardner LLP (57) ABSTRACT

This disclosure relates to an implantable lead for electrical stimulation of an organ and/or for collecting electrical potentials on this organ. The lead comprises a distal termination able to come into contact with the tissues of an organ, the termination comprising an insulating substrate and at least one conductive interface carried by the substrate. The lead further comprises a lead body having at least one bonding conductor connected to a respective conductive interface. The conductive interface comprises at least one deformable conductive wire with a woven, embroidered, braided or knitted configuration for anchoring the deformable wire to the substrate.

8 Claims, 9 Drawing Sheets

(51) Int. Cl.
    *A61B 5/00*           (2006.01)
    *A61N 1/36*           (2006.01)
    *H05K 1/03*           (2006.01)
    *H05K 3/10*           (2006.01)

(52) U.S. Cl.
    CPC ......... *A61N 1/36053* (2013.01); *H05K 1/038* (2013.01); *H05K 3/103* (2013.01)

(58) Field of Classification Search
    USPC ................................................ 607/115–156
    See application file for complete search history.

(56) References Cited

U.S. PATENT DOCUMENTS

| | | | |
|---|---|---|---|
| 2007/0028821 A1 | 2/2007 | Bennett et al. | |
| 2010/0262214 A1* | 10/2010 | Robinson | A61N 1/0551 607/116 |

OTHER PUBLICATIONS

International Search Report and Written Opinion on International Patent Application No. PCT/EP2017/053485 dated Jul. 5, 2017. 9 pages.

\* cited by examiner

IMPLANTABLE LEAD FOR ELECTRICAL STIMULATION AND/OR FOR COLLECTING ELECTRICAL POTENTIALS ON AN ORGAN, INCORPORATING A PASSIVE COMPONENT FUNCTION

CROSS-REFERENCE TO RELATED PATENT APPLICATIONS

This application is a 371 U.S. National Application of International Application No. PCT/EP2017/053485, filed Feb. 16, 2017, which claims the benefit of and priority to French Patent Application No. 1651215, filed Feb. 16, 2016, which is incorporated herein by reference in its entirety.

BACKGROUND

The present invention relates to "active implantable medical devices" as defined by the Directive 90/385/EEC of 20 Jun. 1990 of the Council of the European Communities, and more specifically to devices comprising one or more implantable electrodes applied against an organ to enable electrical stimulation of the latter and/or the collection of electrical potentials on this organ.

The invention will be more particularly described in the context of stimulation of the nerves, especially stimulation of the vagus nerve in the case of therapies called "VNS" (Vagus Nerve Stimulation).

However, this application is given only by way of example and is not limiting in nature, the invention being able to be used for the stimulation/detection of any other organ in fields such as neurostimulation, neurosurgery, cardiology, electrical stimulation of tissue, etc., whenever it is necessary to have implantable electrodes comprising one or more interfaces with biological tissues of a target organ.

In the case of stimulation of the nerves, an essentially flat electrode is generally used, which is wound directly around the external wall of the nerve to be stimulated.

The electrode is provided with conductive interfaces connected to bonding conductors extending along a lead body to an opposite, proximal end coupled to a generator delivering controlled electrical pulses.

In other applications, a tubular electrode is inserted into a vessel so as to press the conductive interfaces as close as possible to the inner wall of the vessel to electrically contact the electrodes of the device with surrounding nerve fibers extending close to the vessel.

In yet other applications, the target organ is comprised of muscle fibers, cerebral tissue, cardiac tissue (e.g. in an application to a defibrillation electrode, etc.).

The invention relates more particularly to the part of the lead implanted against the target organ, hereinafter referred to as "termination" or "distal termination", which makes it possible to keep the electrodes in contact with the target organ or in the close vicinity of this one.

In the particular example of stimulation of the vagus nerve, given the elongated and approximately cylindrical configuration of the nerve, the termination is in the form of a tubular cuff wrapped around the nerve.

As regards the electrodes and the method in which they are produced, several known techniques can be implemented, such as:

Transfer of contacts and crimping to the connecting conductor providing electrical coupling with the pulse generator located at the opposite, proximal end of the lead body;

Making the contacts from a metal sheet held on the surface of the cuff, thus forming an annular contact with the nerve after placing the cuff; or Contact formation by chemical or physical vapor deposition (PVD/CVD) on the surface of a biocompatible organic substrate, this substrate then being fixed to the cuff.

None of these techniques, however, provides high mechanical flexibility, permitting good application of the lead termination against the target organ.

Now, it is highly desirable that this lead termination (typically the cuff that can be wound around the nerve and the electrodes carried by this cuff) perfectly matches the surface of the target organ. Indeed, this close contact is necessary to lower the electrical stimulation threshold and thus avoid the application of too high currents which could induce undesirable side effects and in any event would shorten the lifespan of the implantable generator.

Another important condition to be respected is that, from a mechanical point of view, the lead termination applies to the target organ only a minimum of stresses, both at the time of implantation and after, in spite of the possible displacements of the organ, of its possible swelling, etc.

Mechanical stresses exerted globally (cuff too tight) or locally (at an outgrowth of the lead termination in contact with the nerve) would in fact tend to cause inflammation of the target organ, which is of course damaging.

These conditions are difficult to fulfill with the existing lead terminations, in particular because of the inevitable stiffness of the cuff (or similar interface), even if the latter is made of a very flexible material: indeed, because of its elastic character, this cuff necessarily exerts a mechanical constriction force on the nerve, effort which is moreover not uniform and can generate locally relatively important constraints. Moreover, the conventional electrodes all involve the deformation of metal parts adding their own stiffness to that of the cuff. Finally, the cuff defines an internal contact surface which is inherently a developable surface, whereas the external surface of the target organ is a non-developable surface: even if the nerve has an approximately cylindrical shape, it is only an approximation and in practice it will only imperfectly contact the cuff, with contact regions creating mechanical stresses on the nerve and non-contact regions which are ineffective in terms of electrical stimulation.

In order to overcome these disadvantages, it has been proposed, instead of using inserts or deposited contacts, to produce the conductive interface intended to come into contact with the target organ in the form of one or more elongate conductive wires assembled to a substrate by weaving, embroidering, braiding or knitting. The substrate with the interface thus produced can be used as such as a termination, or it may be added to an additional support, for example on a self-winding silicone cuff.

The conductive interface can then be applied exactly against the target organ, for example to wrap around a nerve, with relative deformability enabling the organ irregularities or dimensional changes to be absorbed (swelling, etc.) thereof.

Moreover, this configuration offers a very great diversity in the geometries of contacts that it is possible to produce, by weaving the conductive wire or wires in a well-defined method to maximize the desired effects and/or to define precise stimulation sites on the termination.

The aim of the present invention is, on the basis of such a structure, to improve the electrical performance of the interface intended to come into contact with the target organ and to be able to incorporate components or circuits at the interface near the detection/stimulation site.

Indeed, in many applications, it is desirable to have electronic components located as close as possible to the tissues to be excited by an electrical potential or by the injection of a current, or on which it is desired to collect an electrical potential.

A typical example is the securing of implantable devices (generators and their associated leads) when the patient is subjected to magnetic resonance imaging (MRI or MRI). Indeed, an MRI examination is currently contraindicated for patients with an implanted pacemaker due to the very high electromagnetic field produced by the MRI device: this field is in particular capable of inducing in the lead parasitic currents and evoked potentials which can be deleterious by Joule or else undesirable effect if an induced potential or current recruits the nerve or cardiac cells located in the vicinity.

To mitigate this risk, it is possible to insert in the current loop a resonant circuit such as a plug circuit tuned to the RF frequency generated by the MRI imager. It will be understood that such a circuit must be placed as close as possible to the elements to be protected, and therefore as close as possible to the lead termination for its efficiency to be maximum.

In general, when it is desirable electronic components are placed near a lead end, conventional electronic components (resistance, capacitor, inductance, etc.) are used, the isolation and biocompatibility of which are more or less problematic and whose integration at the lead termination involves a delicate design of the components associated with the conductive interface.

SUMMARY

The starting idea of the invention is to produce these electronic components at the same time as the weaving, embroidering, braiding or knitting of the conducting wires is carried out, in the case of a lead termination, Conductive interface is performed as explained above.

More precisely, the invention proposes a technique making it possible to incorporate into the substrate one or more passive electrical components made by the same weaving, embroidering, braiding or knitting technique directly at the electrode or elsewhere of the lead termination or more generally at each point wherein a wire of the conductive interface is anchored to the substrate by the particular technique used.

Such a configuration has several advantages:

From the biocompatibility point of view, if the conductors and the external geometry of the interface are biocompatible, then the electronic circuit made from the components incorporated in the termination will also be biocompatible;

from the deformation point of view, the deformability properties making it possible to absorb the irregularities of the organ or the dimensional changes thereof, resulting from the particular technique used, will also be applicable to the additional components integrated at the termination of lead;

Finally, from the point of view of the location of the electronic circuit made from the incorporated components, it is possible to place this circuit as close as desired to an area of interest, for example, as close as possible of the electrodes for stimulation or electrical potential detection.

These passive components may in particular be, as will be described later: resistance, capacitor, RF antenna, inductance, transformer or any combination of the preceding components.

More precisely, the invention proposes for this purpose an implantable lead for the electrical stimulation of an organ and/or the collection of electrical potentials on this organ comprising, in a manner known per se:

A distal termination capable of coming into contact with the tissues of the organ, this termination comprising an insulating substrate and at least one conductive interface carried by the substrate; and A lead body comprising at least one connecting conductor connected to a respective conductive interface.

Typically:

The conductive interface comprises at least one deformable conductive wire;

The conductive interface comprises a woven, embroidered, braided or knitted configuration for anchoring the deformable wire to the substrate; and Said woven, embroidered, braided or knitted configuration comprises a pattern conferring on said at least one deformable conductive wire a passive component electrical function.

According to various advantageous subsidiary characteristics:

The substrate is a non-elastically deformable substrate and the conductive interface is devoid of an additional elastically deformable support incorporating the substrate or adjoining the substrate;

The passive component electrical function is a resistive function, the pattern comprising a zigzag pattern of the deformable conductive wire on the substrate;

The passive component electrical function is a resistive function, at least a portion of the deformable conductive wire being an intrinsically resistive portion in the region of the pattern;

The passive component electrical function is a capacitive function, the deformable conductor wire being interrupted in the region of the pattern and being configured on the substrate to form there two interconnected, non-electrically connected parts extending together along the other leaving a coupling gap forming a capacitor dielectric therebetween;

The passive component electrical function is an antenna function, the deformable conductive wire comprising in the region of the pattern a free distal end configured on the radiofrequency radiating element substrate;

The passive component electrical function is an inductive function, the deformable conducting wire being wound on either side of the plane of the substrate in the region of the pattern or else flat on the substrate in the region of the pattern. In the first case, at least one additional wire of non-electrically connected ferromagnetic material extending in the region of the pattern inside the coiled part of the deformable wire and forming the core for the inductive component may advantageously be provided. In this method, it is possible to associate two distinct configurations of inductive, not electrically connected, component, wound on at least one additional wire of common ferromagnetic material forming a transformer coupling core;

The lead comprises a plurality of inductive, capacitive and/or resistive components combined in a stop filter tuned to at least one RF frequency of an IRM imager.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

Various embodiments of the invention will now be described.

Figures 1, 2, 3:
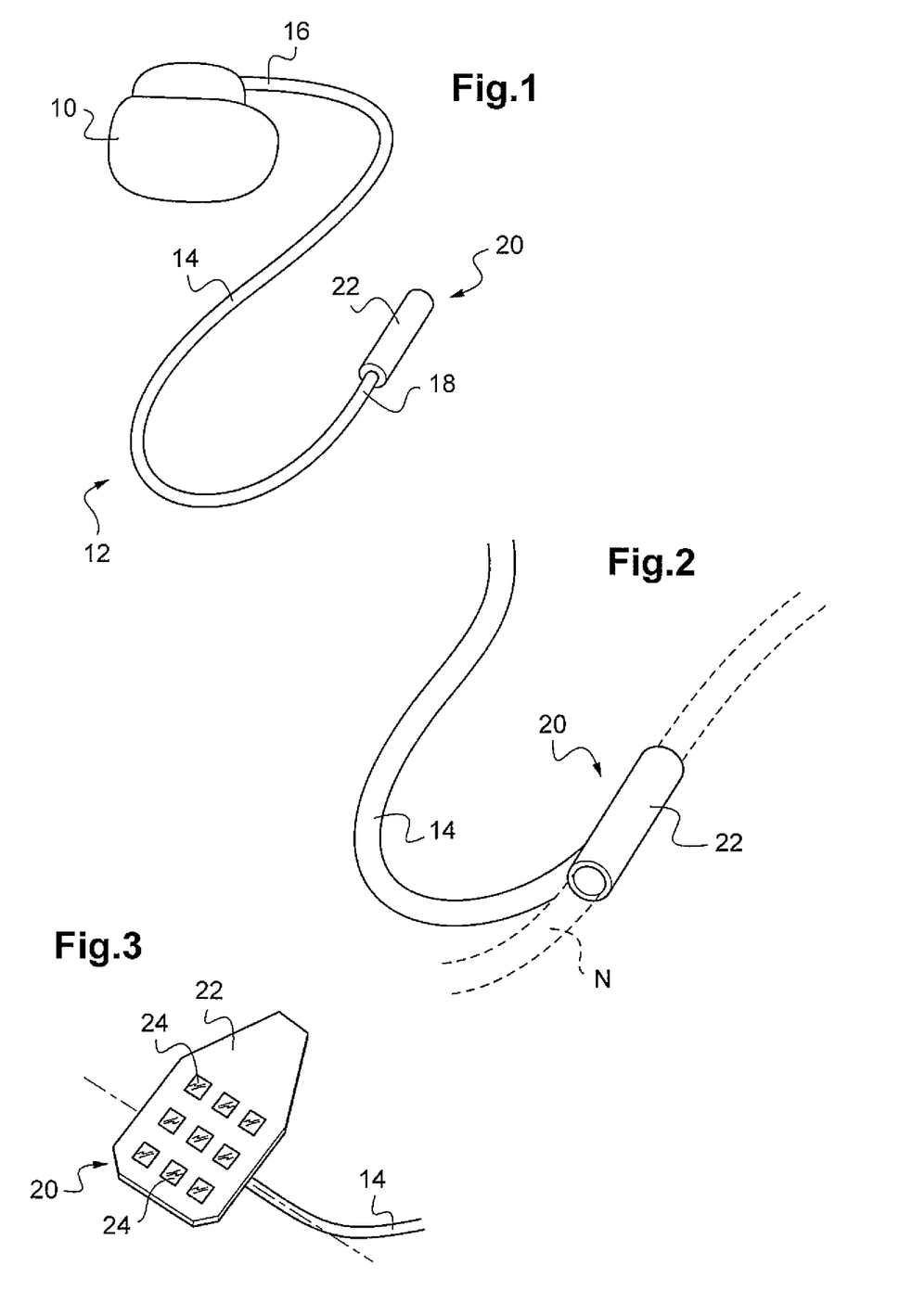
FIG. 1 illustrates the set of elements of a VNS stimulation device.
FIG. 2 more specifically shows an example of termination wound around a nerve of the device of FIG. 1.
FIG. 3 illustrates, in the unwound form before implantation, a self-wounding cuff according to the prior art, constituting the termination component of FIG. 2.

FIG. 1 illustrates all the elements of a VNS stimulation device.

This system comprises an electrical pulse generator 10 connected to one or more lead(s) 12 for the delivery of the stimulation pulses produced by the generator and/or the collection of electrical potentials which will be analyzed by the generator.

The lead 12 comprises a flexible elongate tubular lead body 14, connected at its proximal portion 16 to the generator 10, generally via a plug-in connector, and having at its distal portion 18 an element, hereinafter referred to as "termination" 20 capable of coming into contact with the tissues of an organ to be stimulated.

The lead body 14 includes a number of independent electrical conductors, hereinafter called "bonding conductors" making it possible to connect various electrodes of the termination 20 to homologous terminals of the generator 10.

These bonding conductors are generally wound inside the lead body in a helical configuration so as to preserve the flexibility of the lead while retaining sufficient strength properties to avoid breakage of a bonding conductor.

The termination 20 may take several forms, and a configuration in which the termination is wound around a nerve, typically the vagus nerve, will be described hereinafter.

FIG. 2 illustrates an example of a conventional termination, made by means of a self-winding cuff 22 around the nerve N so as to best match the shape of the latter.

FIG. 3 illustrates, in unfolded form prior to implantation, the cuff of the termination of FIG. 2.

This cuff 22 is typically made from a sheet of elastically deformable material, for example a silicone, carrying a plurality of electrically conductive pads (hereinafter "conductive interfaces") intended to be applied against a precise stimulation site of the organ to be stimulated. Each of the conductive interfaces 24 is connected to a respective current conductor within the lead body 14 to be connected to a corresponding terminal of the generator, at its proximal side. The deformable sheet intended to form the cuff 22 is advantageously prestressed so as to permit its self-winding from an initial position wherein the sheet is held under stress in the deployed state (configuration of FIG. 3) to a final position wherein the sheet is freely wound spirally forming a cuff around the organ (configuration of FIG. 2), the side carrying conductive interfaces 24 then bearing against the outer surface of the nerve N. Such a self-winding cuff configuration is, for example, disclosed in U.S. Pat. No. 4,602,624 A.

Lead Termination and Conductive Interfaces Usable for the Implementation of the Invention The invention is placed in the context of another type of lead termination and interface, of which several possible embodiments will be described beforehand.

Figure 4:
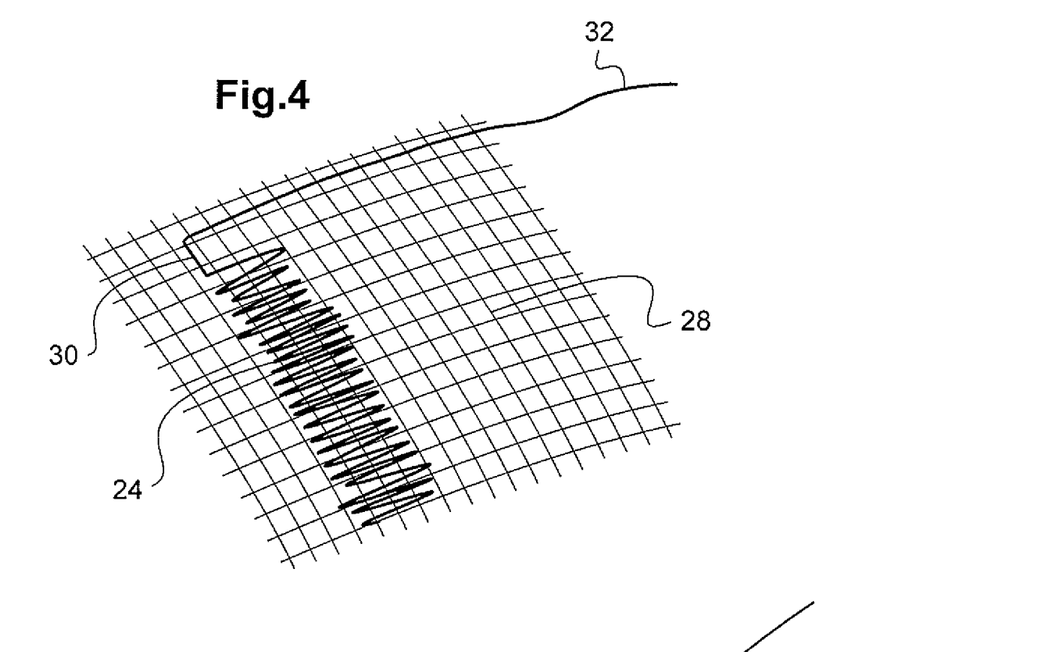
FIG. 4 illustrates an embodiment of a termination usable for the implementation of the present invention.

Thus, FIG. 4 illustrates a first embodiment of the interface that can be used to implement the teachings of the invention.

Each of the conductive interfaces 24 is made from a deformable conductor wire 30 which is at least partially stripped and which in the example illustrated is anchored to a substrate 28 by embroidering or by another similar technique (weaving, braiding, knitting, etc.). This conductor wire 30 is connected to a respective bonding conductor 32. The set of bonding conductors 32 of the termination then runs inside the lead body to the distant proximal-side generator.

In the example of termination illustrated in FIG. 4, the conductor wire 30 is constituted by a direct extension of the bonding conductor and it is embroidered on the substrate 28. The wire remaining after embroidering is preserved and constitutes the bonding conductor 32, and there is thus no solution of continuity between these two elements.

Figure 5:
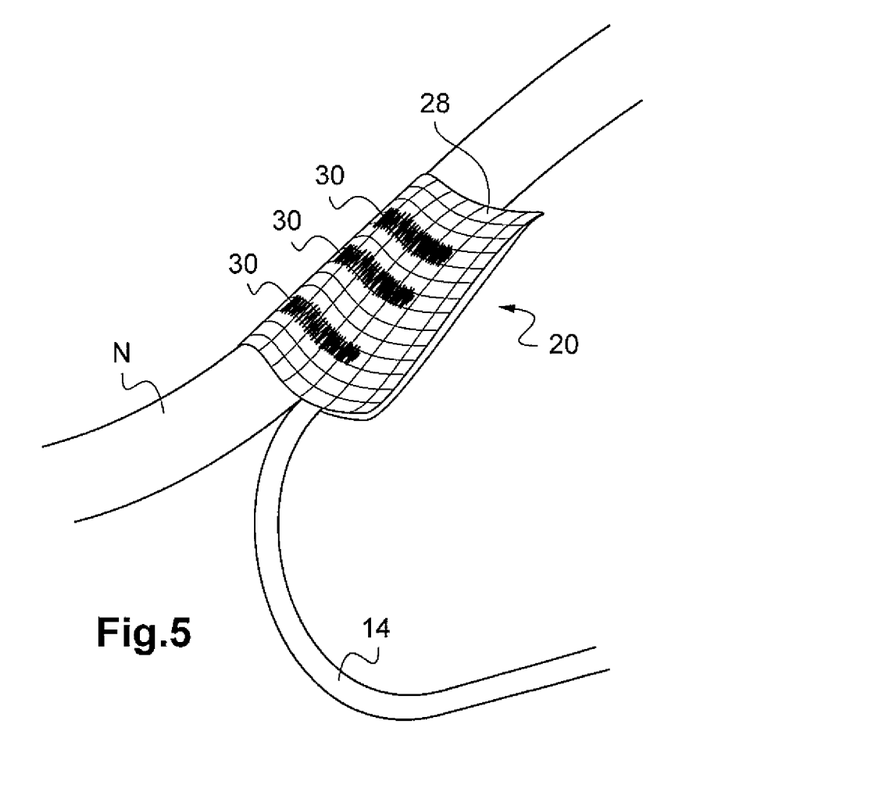
FIG. 5 illustrates the termination of FIG. 4 applied against the target organ.

FIG. 5 illustrates the termination of FIG. 4, applied against the target organ. As can be seen, the insulating woven substrate 28, which is very flexible and deformable, can be used in the manner of gauze applied and wrapped around the nerve N. The regions where the conductor wires have been embroidered form electrodes and the protruding part of the substrate 28 (part extending approximately in an axial plane) adjoins the lead body 14, which is therefore not directly in contact with the nerve N, which therefore dramatically reduces the transmission to the nerve N of stresses likely to be received by the lead body 14.

In general, the substrate 28 can be presented in different forms, depending on the specificities of the organ to be stimulated.

Depending on the case, the substrate 28 may be made from: an isotropic homogeneous material; an anisotropic homogeneous material; a generally isotropic short fiber material; a generally anisotropic short fiber material; a unidirectional woven material; a bidirectional woven material; a multidirectional woven material; or any combination thereof.

As regards the actual material of the substrate, it may be: an active material such as nitinol; a biocompatible polymer material such as Dacron, silicone, parylene, polyethylene, polyurethane or polyimide; a conductive material such as MP35N, platinum, platinum-iridium alloy, stainless steel such as 304 or 316; a resorbable material; a soluble material such as glucose; or any combination thereof.

The substrate may be reversibly deformable or not, with or without input of energy of mechanical, thermal or chemical origin or other source of energy external or internal to the substrate.

In the case of a woven substrate, the weft and warp yarns which compose it may or may not move with respect to one another. Still in the case of a woven substrate, the wires can be woven at a right angle or at another angle (60°, 45°, 30°, 15° or any other angle). On the other hand, the weave of the weaving can be of any known type such as twill, satin, taffeta or any other weave.

Still in the case of a woven substrate, it is possible to use a fabric of conductor or not, insulated or non-insulated, wires. If conductor wires incorporated in the substrate are used, they may be stripped along their entire length, or only in certain places. In the latter case, the stripping may be carried out mechanically by laser ablation, chemical ablation, abrasion or any other method enabling at least some of the conductive material of the wire to be exposed to the external medium. It will be noted that it is not necessary for all of the weft or warp yarns to be conductive, but that this property may be reserved for only some of the weft and/or warp threads, the others being conventional non-conductor wires, forming the substrate.

Finally, again in the case of a woven substrate, the conductive wires forming the conductive interface may be incorporated into the weft forming the substrate at the time of weaving or knitting thereof or added to the substrate in a subsequent step, for example by embroidering, the conductor wire then passing through the substrate and being thus mechanically anchored to the latter.

The conductive interface intended to come into contact with the tissues of the organ to be stimulated is thus sewn, woven or embroidered on the substrate. The positioning and the extent of the conductive interface can then be judiciously chosen and oriented in such a way that the substrate remains flexible and/or extensible, the termination thus remaining globally flexible and/or extensible, this property being necessary to best match the organ to be stimulated and to adapt itself to the possible deformations of the latter.

The conductive interface may comprise a substrate with a weaving, braiding, embroidery or any other suitable method which is suitably chosen, equipped with woven, embroidered, sewn electrodes or assembled by any other similar method capable of conforming to non-developable complex shapes.

Figure 14:
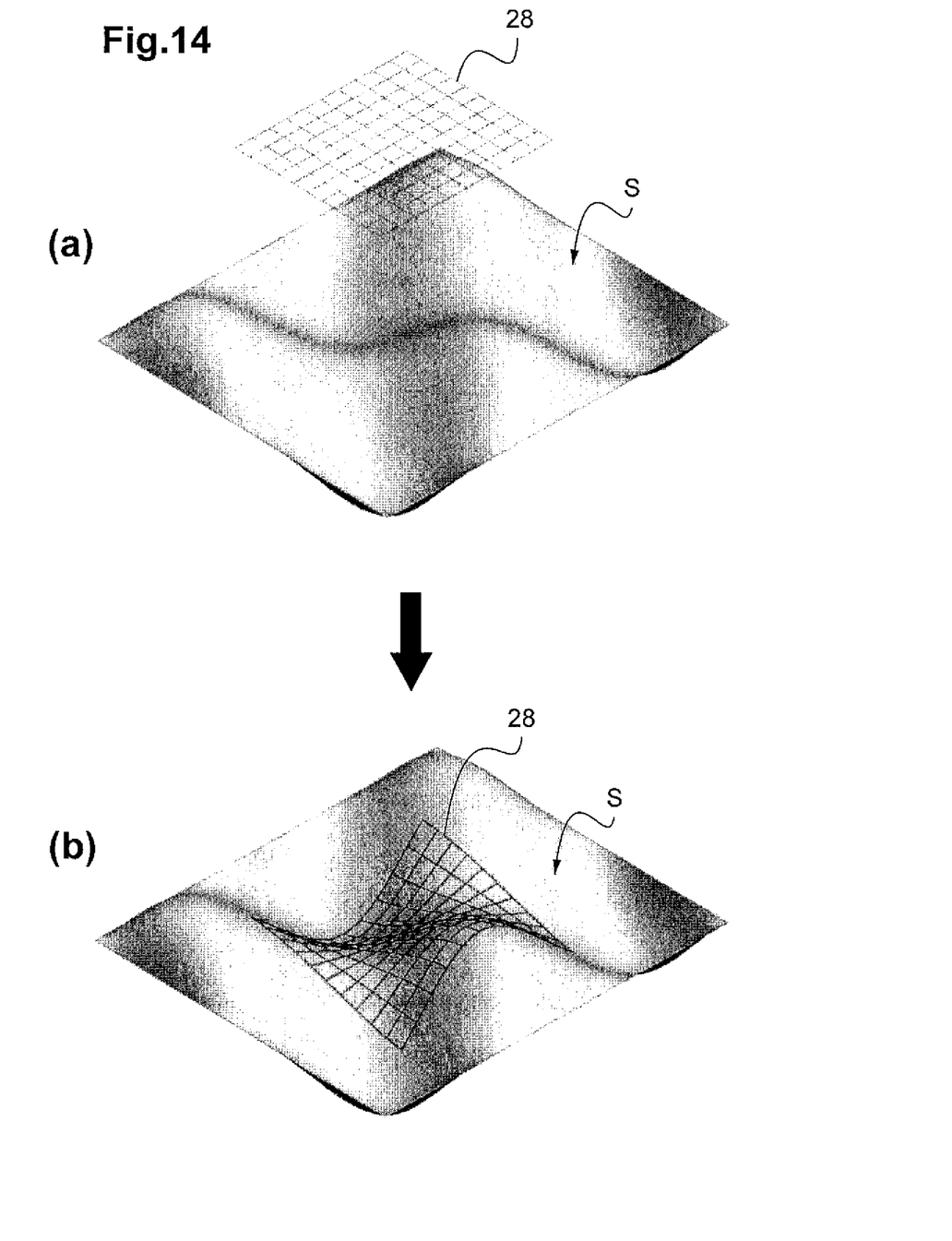
FIG. 14 illustrates the substrate before and after its application to a complex surface.

In FIG. 14, the substrate 28 is illustrated in (a) before its application to the receiving surface S, and (b) after its application: it can be seen that the substrate 28 perfectly matches the complex shape S by allowing its constituents (weft and warp yarns, etc.) to reposition themselves in relation to one another. There is thus no permanent induced effort on the biological tissues, whilst maintaining optimal contact.

The conductive wire constituting the conductive interface may be an insulated or non-insulated, single-stranded or multi-stranded wire. If it is insulated, the conductive core will be exposed to the external environment by laser ablation, chemical ablation, manual cutting or any other means for stripping the conductor.

In the embodiment illustrated in FIG. 4, the conductive wire constituting the conductive interface of the termination was an extension of the bonding wire, which is then mechanically bonded to the substrate by an appropriate means (sewing points, glue, etc.).

In other embodiments, shown in FIGS. 6-13 and described hereinafter, the lead wire is distinct from the bonding wire, and these two elements are electrically connected at a coupling point. This makes it possible, in particular, to use a very fine wire for the conductor wire constituting the conductive interface, the bonding wire being thicker.

As far as the bonding conductor is concerned, if it is of a generally lengthy nature, it may be at least partly mechanically bonded to the substrate by stitching, weaving, embroidering directly or with a third material. The points thus formed may be continuous, spaced regularly or spaced irregularly.

The bonding conductor, or a portion thereof, may be mechanically bonded to the substrate by adhesive, solder, solder, local fusion, or any other process utilizing the cohesive or adhesive properties of a third or autogenous material.

In the case of a bonding conductor of a generally lengthy nature and with a planar substrate, it is possible to connect the bonding conductor to the substrate by crossing one or more times the plane formed by the substrate, that is to say using the method of a sewing point passing alternately over and under the substrate.

Still in the case of a conductor of a generally lengthy nature and with a planar substrate, a method for mechanically bonding it, in whole or in part, with the substrate consists in making one or more turns generally in the plane of the substrate, of more or less important curvature.

If the bonding conductor is of a generally lengthy nature, this conductor or a part thereof may be mechanically bonded to the conductor wire constituting the conductive interface by welding, brazing, bonding, wedging, embroidering, weaving, braiding, sewing, crimping, binding or by any other assembly method.

If the bonding conductor has helical nature and the substrate is planar, a method for mechanically binding it or bonding a part thereto may cause one or more turns of one or more strands of the helix to be deformed from so as to render these strands parallel to the plane of the substrate, to which they can then be mechanically bonded over all or part of their length by welding, soldering, gluing, wedging, embroidering, weaving, braiding, sewing, crimping, binding or by any other method.

The conductors, whether used to make the bonding conductors or the electrode conductors, can be of several types. They may either be naturally biocompatible or coated with biocompatible materials such as 35NLT, MP35N, 304 stainless steel, 316L stainless steel, platinum, platinum-iridium alloy, or any other biocompatible metal, or any other biocompatible conductor or semiconductor material. These conductors may or may not be insulated. If this is the case, the isolation material may be, for example, ethylene tetrafluoroethylene (ETFE).

Figures 6, 7, 8:
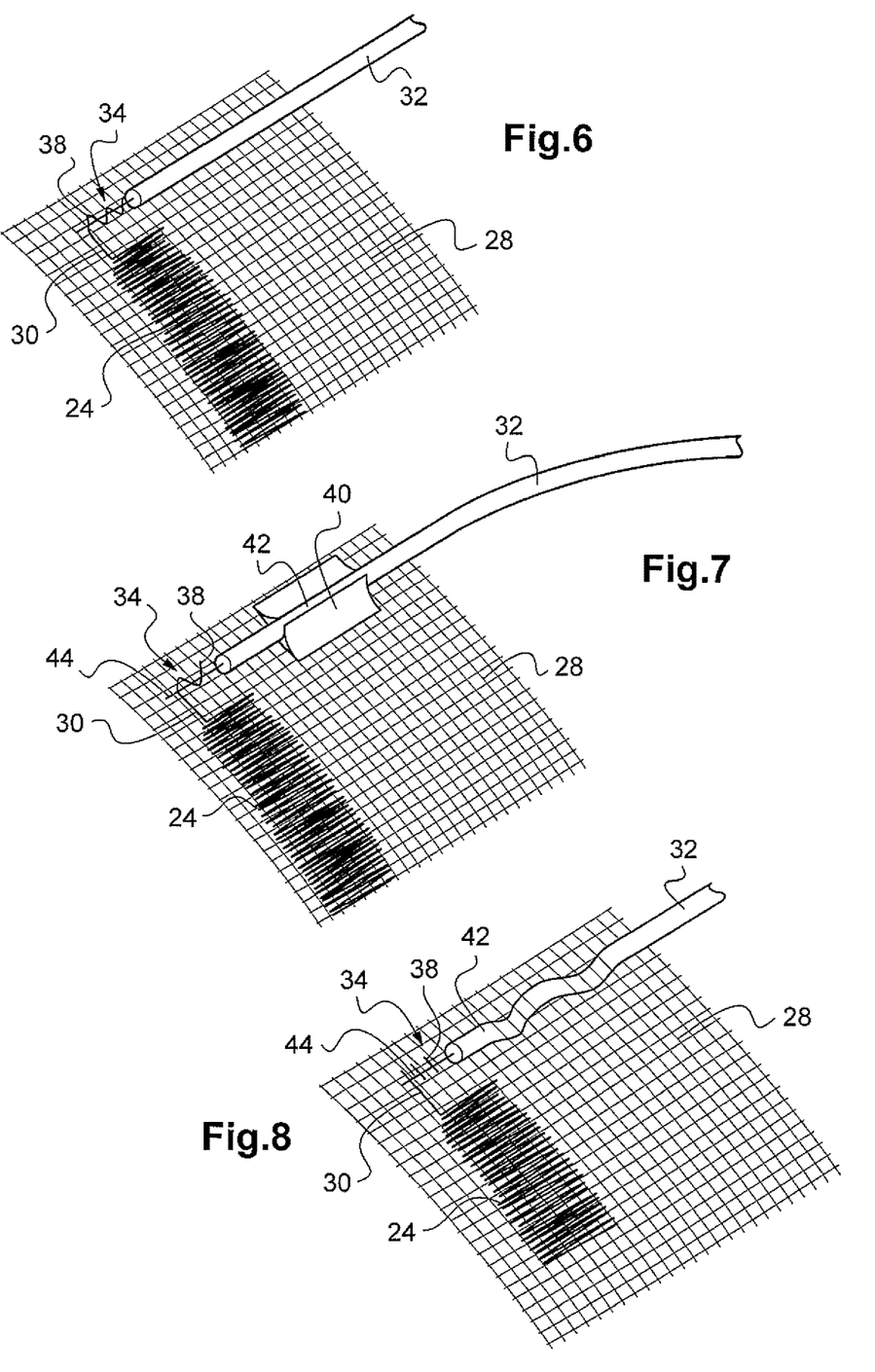
FIG. 6 illustrates a first example of mechanical attachment of the bonding conductor to the substrate.
FIG. 7 illustrates a second example of mechanical attachment of the bonding conductor to the substrate.
FIG. 8 illustrates a third example of mechanical attachment of the bonding conductor to the substrate.

FIG. 6 illustrates a first example of mechanical attachment of the bonding conductor to the substrate, at a coupling point 34.

In this example, the bonding conductor 32, which is electrically connected to the embedded conductor 30 on the substrate 28, is mechanically anchored to the latter by sewing points 38.

FIG. 7 illustrates a second example of mechanical attachment of the bonding conductor to the substrate.

In this example, the bonding conductor 32 is anchored to the substrate 28 by means of an adhesive point 40 surrounding the insulator 42 (or the stripped portion) of the bonding conductor 32 in a region close to the coupling point with the conductor wire 30, the conductive core 44 of the bonding conductor being, as in the example of FIG. 6, mechanically anchored to the substrate 28 by sewing points 38, so as to ensure recovery of the possible stresses undergone in the region of the coupling with the conductor wire 30.

FIG. 8 illustrates a third example of mechanical attachment of the bonding conductor to the substrate.

In this example, the bonding conductor 32 is secured to the substrate 28 by weaving with it, alternately passing below and above the plane of this substrate. The anchoring of the bonding conductor 32 to the substrate 28 is thus ensured in a purely mechanical method, and thus without use of a third material as in the case of the bonding 40 of FIG. 7. For the rest, the embodiment is identical to that of FIG. 7, the stitches 38 for anchoring the conductive core 44 to the substrate 28 being situated in the vicinity of the connection of the latter with the conductor wire 30.

Figure 9:
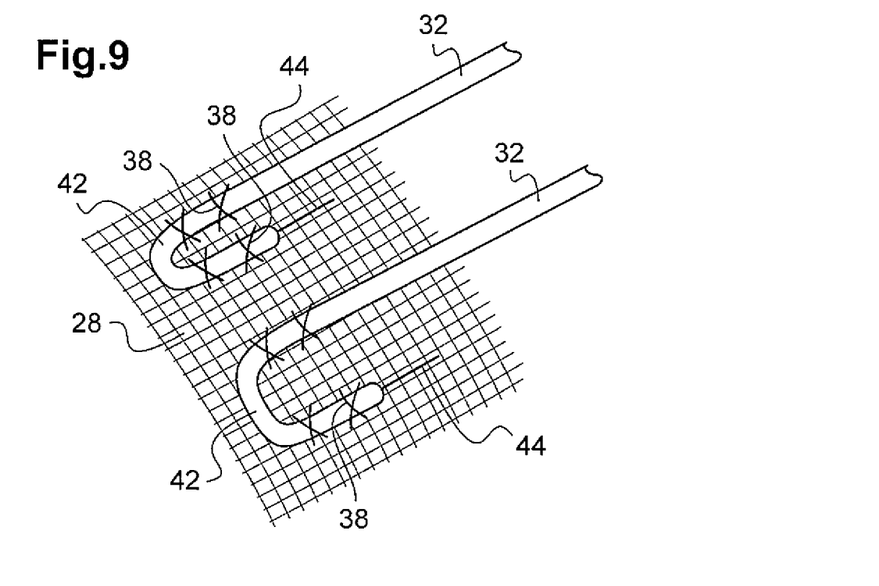
FIG. 9 illustrates a fourth example of mechanical attachment of the bonding conductor to the substrate.

FIG. 9 illustrates a fourth example of mechanical attachment of the bonding conductor to the substrate.

In this example, the bonding conductor 32 terminates in a U-shape in its distal end portion just prior to the emergence region of the conductive core 44. The insulating sheath 42 (or stripped portion) of the bonding conductor 32 is then secured to the substrate 28 by sewing stitches 38 made on each of the branches of the U.

Figure 10:
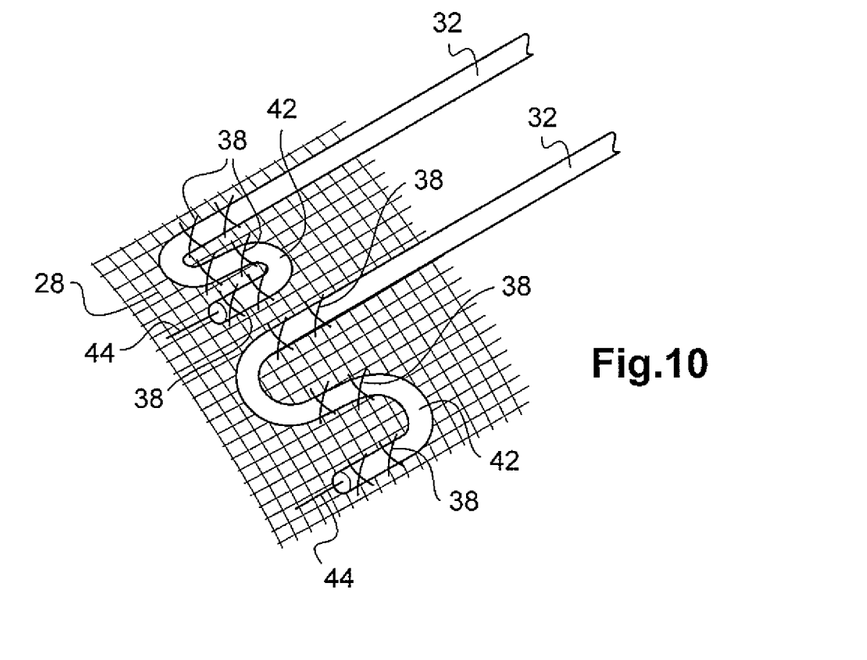
FIG. 10 illustrates a fifth example of mechanical attachment of the bonding conductor to the substrate.

FIG. 10 illustrates a fifth example of mechanical attachment of the bonding conductor to the substrate.

In this example, the terminal portion of the bonding conductor 32 is S-shaped in its distal end portion just prior to the emergence region of the conductive core 44. The insulating sheath 42 (or the stripped portion) of the bonding conductor 32 is then secured to the substrate 28 by sewing points 38 made on each of the branches of the S.

Figure 11:
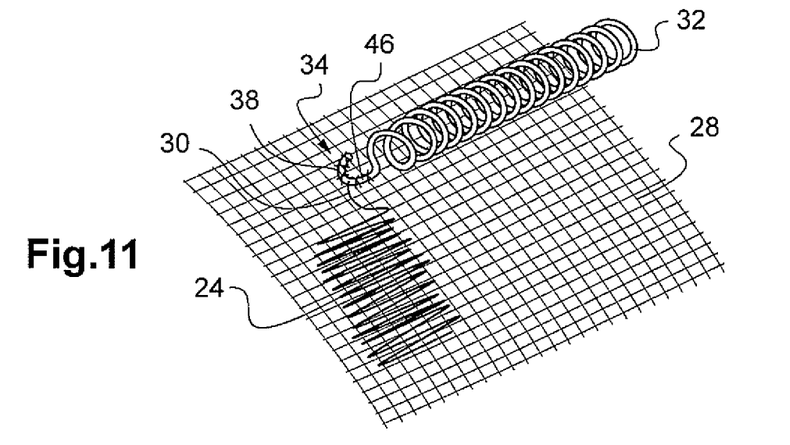
FIG. 11 illustrates an embodiment in which the connecting conductor has a helical shape.

FIG. 11 illustrates an example in which the bonding conductor 32 has a helical shape, typically corresponding to the case of a helical bonding conductor emerging from the inside of the lead body and which is not straightened in its end portion. The free end of the bonding conductor is then configured, for example, in the form of a loop or hook 46, which is secured to the substrate 28 by sewing stitches 38 in the region situated in the vicinity of the coupling with the conductor wire 30 which forms the conductive interface of the lead termination.

Figure 12:
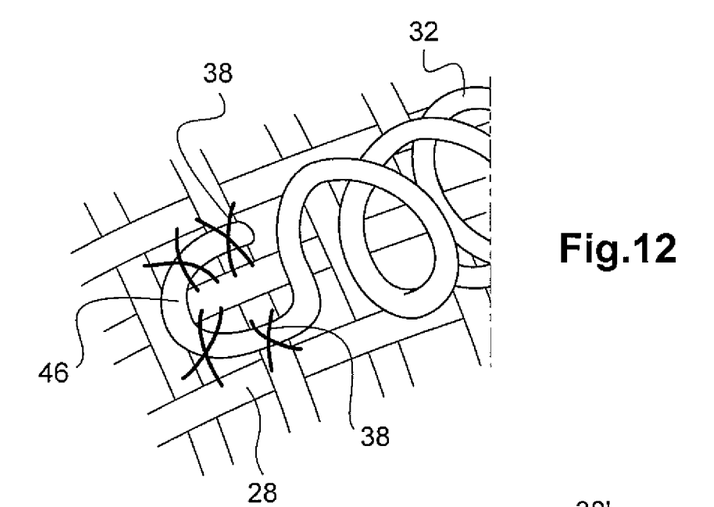
FIG. 12 is a greatly enlarged detail view of the end of the connecting conductor of FIG. 11.
Figure 13:
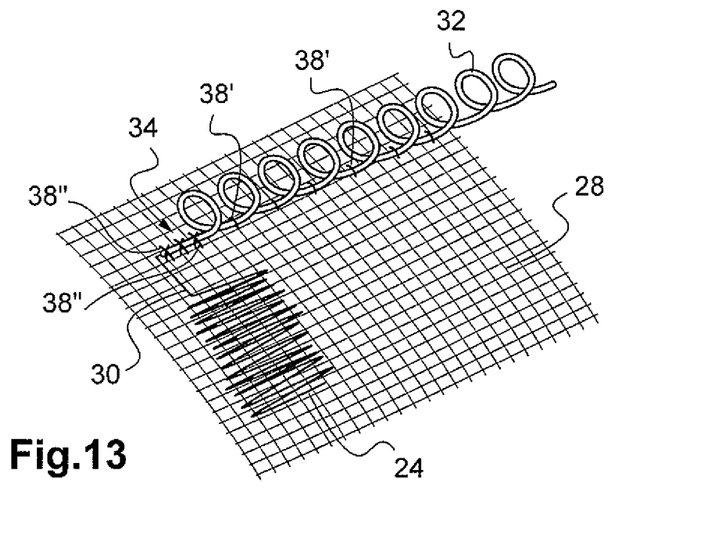
FIG. 13 illustrates another example of attachment of a helical bonding conductor to the substrate.
Figure 15:
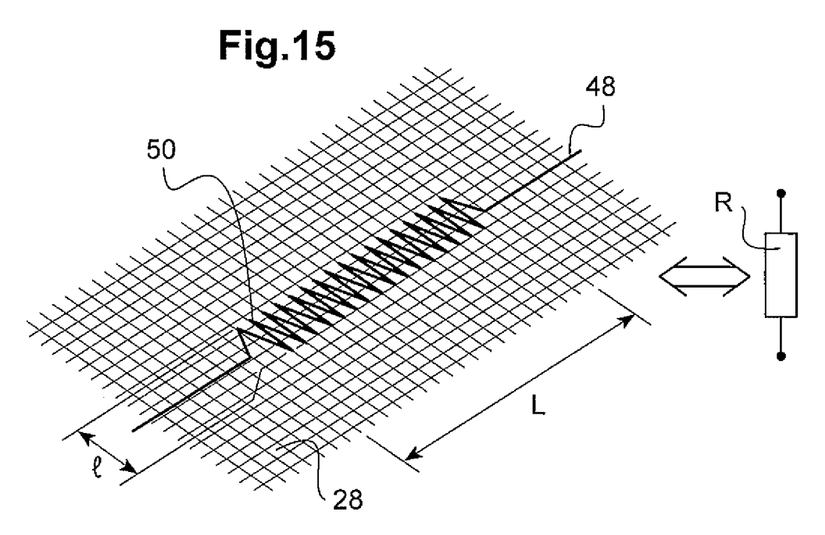
FIG. 15 illustrates a first embodiment of a passive component according to the invention, wherein the component is a resistor.

FIG. 12 is a greatly enlarged detail view of the end of the bonding conductor of FIG. 15, showing the hook 46 and the stitches 38 for its attachment to the substrate 28.

FIG. 14 illustrates yet another method of attaching a helical bonding conductor to the substrate.

In this example, the last turns of the connecting conductor 32 are anchored to the substrate by stitches 38' in the region wherein these turns come into contact with the latter, the end portion of the bonding conductor 32 being anchored to this same substrate by other stitches 38" in the vicinity of the coupling zone with the conductor wire 30 intended to form the conductive interface of the termination.

Incorporation of Passive Components
In the Lead Termination

The present invention relates to the incorporation of passive components in a lead termination of the type described above.

The invention proposes a technique making it possible to incorporate into the substrate that has been described one or more passive electrical components, produced by the same weaving, embroidering, braiding or knitting technique, these components being advantageously produced at the same time as the conductor wires forming the electrodes of the lead are woven, embroidered, plaited or knitted.

Figure 16:
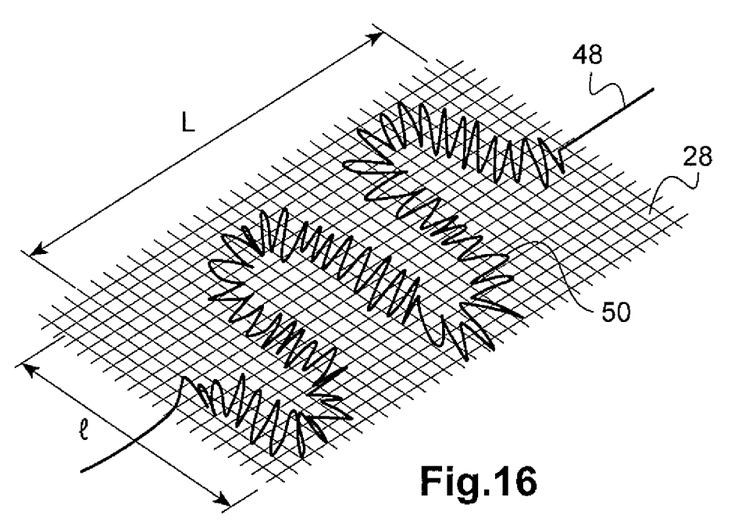
FIG. 16 illustrates an alternative embodiment of the embodiment of FIG. 15.

In FIGS. 15 and 16, an example is illustrated in which the passive component is a resistor R.

For this purpose, the conductor wire 48 is knitted in a zigzag pattern 50 over a length L and a width 1 directly on the substrate 28. The resulting increase in the length of the wire 48 produces between the two end regions of the pattern 50 a voltage drop equivalent to that of an electrical resistance R.

Another technique for producing the resistive component, alternatively or in addition to the preceding one, consists in using an intrinsically resistive conductor because of its dimensions (for example a wire of very small diameter), or by choosing for this wire a material having a specific resistivity (MP35N steel, platinum, platinum-iridium 90/10 alloy for example).

FIG. 16 illustrates an alternative embodiment of the embodiment of FIG. 15 wherein the conductor wire 50 is folded into a double zigzag so as to maximize its length with a reduced nip L×1 on the surface of the substrate 28.

Figure 17:
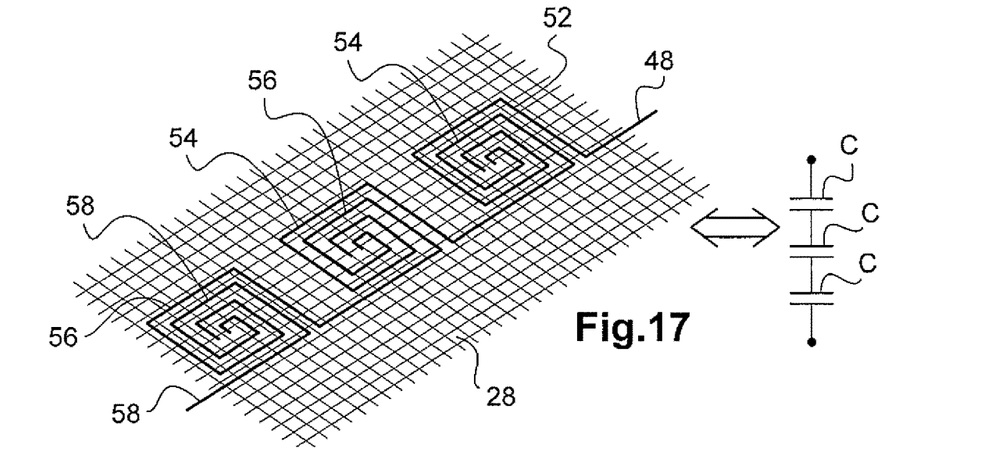
FIG. 17 illustrates a second embodiment of a passive component according to the invention, wherein the component is a capacitor.
Figure 18:
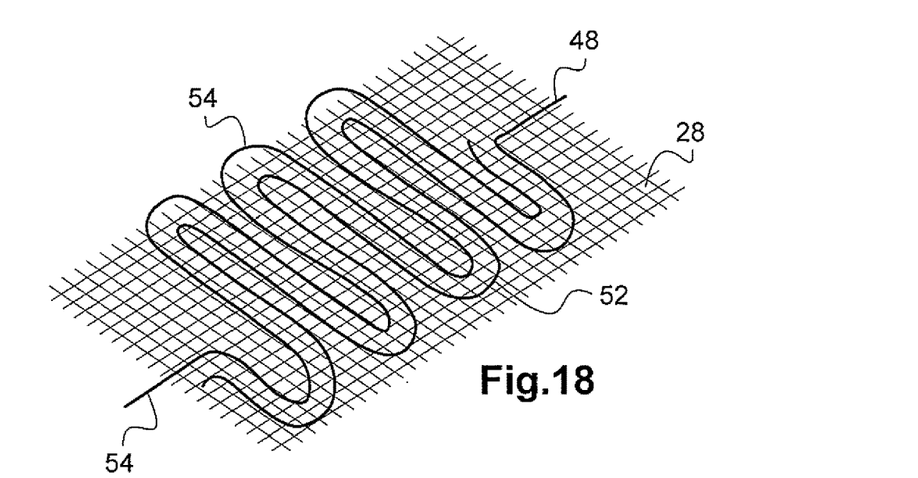
FIG. 18 illustrates an alternative embodiment of the embodiment of FIG. 17.

FIGS. 17 and 18 illustrate an embodiment wherein the component is a capacitive component, with in the example illustrated three capacitors C configured in series.

For this purpose, the conductor wire 48 is interrupted in the region of the pattern and configured to form two non-electrically interconnected interlocking loops 52, 54 extending together along the other leaving a coupling interval forming, due to the proximity of the conductors, a capacitor dielectric providing capacitive properties to the two elements 52, 54 which in turn constitute the armatures of the capacitor C.

It is thus possible to provide several wire sections 52, 54, 56, 58, coupled together by respective loops 52+54, 54+56, 56+58, so as to have a plurality of capacitors connected in series, with an increased voltage resistance.

Another technique for producing a capacitive component consists in using an intrinsically capacitive conductor, such as a conductor wire with an insulating sheath on which a conductive deposit has been formed, with a contact made on this conductive deposit: there are thus two electrically insulated terminals but having capacitive properties between them.

FIG. 18 illustrates an alternative embodiment of the embodiment of FIG. 17, wherein the two non-electrically interlocked loops 52 and 54 are zigzag-shaped so as to maximize the surface of the opposing reinforcements, while maintaining a reduced nip on the surface of the substrate 28.

Figure 19:
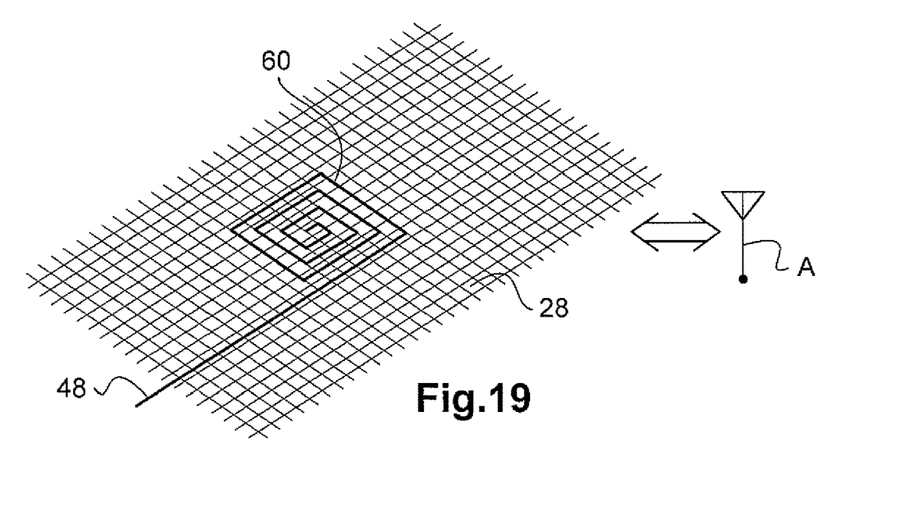
FIG. 19 illustrates a third embodiment of a passive component according to the invention, wherein the component is an RF antenna.

In FIG. 19, an embodiment is illustrated wherein the wire 48 is configured to perform an antenna function A, for example a wireless RF antenna with a remote, implantable or external device. The conductor 48 comprises for this purpose a free distal end 60 configured in a loop to form a radiating element capable of capturing/emitting the radiofrequency electromagnetic field.

This antenna can be used in particular for RF telemetry functions in the MICS (Medical Implants Communication Systems) bandwidth 402-405 MHz, MEDS (Medical External Device Service) bandwidth 400-407 MHz or ISM (Industrial, Scientific and Medical) bandwidths 433-434 MHz, 863-870 MHz, 902-928 MHz and 2.4 GHz used by medical devices, or in 2.4 GHz or 5 GHz Wi-Fi bands or 2.4 GHz Bluetooth. The antenna can also be used for wireless transmission of energy or data, for example inductively. For example, the implantable generator 10 can serve as a source of energy.

The tuning capacitor of the antenna resonant circuit may in particular be a component integrated into the substrate, produced according to the techniques described above with reference to FIGS. 17 and 18.

Figure 20:
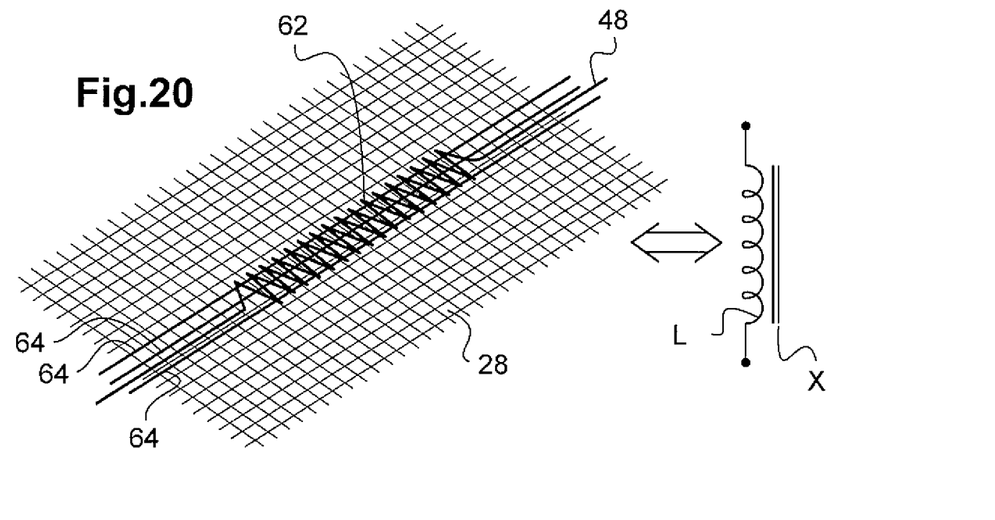
FIG. 20 illustrates a fourth embodiment of a passive component according to the invention, wherein the component is an inductor.

FIG. 20 illustrates an embodiment wherein the passive component is an inductance L.

For this, the conductor 48 is wound on itself in a region 62 of the substrate, the wire being in the illustrated example wound on either side of the plane of the substrate 28. The inductive nature of this component can be increased in placing or replacing a wire in the substrate 28 (e.g, a weft yarn) by one or more wires 64 of a material having ferromagnetic properties (e.g, a soft iron wire) so as to provide a function similar to that of a core L of a conventional inductance.

Another configuration of the pattern 62 providing an inductive function can be obtained by a winding of the conductor wire 48 made in the plane of the substrate, for example with a spiral shape, the axis of the inductance then being perpendicular to the plane of the substrate instead of being contained in the plane of the substrate as in the case illustrated in FIG. 20.

Figure 21:
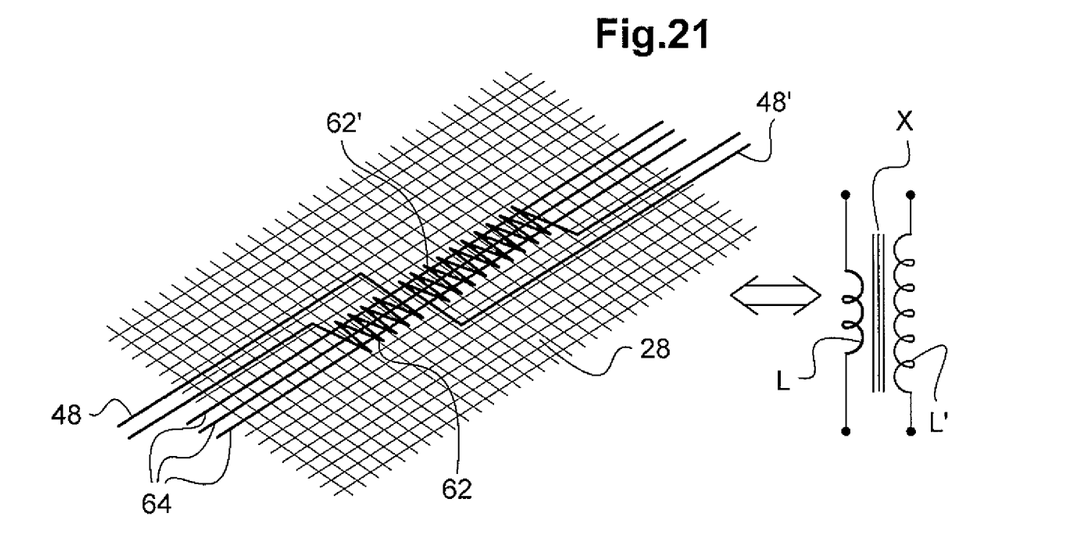
FIG. 21 illustrates a fifth embodiment of a passive component according to the invention, wherein the component is a transformer.

The technique used in FIG. 20 can be used to make a transformer, as shown in FIG. 21.

To this end, two wound patterns 62, 62' are provided, corresponding to respective conductors 48, 48', arranged in the extension of each other on wires 64 forming a common core X. The mutual coupling between the two inductances L and L' formed by the respective patterns 62 and 62' gives an AC/AC transformer which can act as a voltage step-up or depressor, located at near as possible of the delivery electrodes a neurostimulation signal or of collect of the electrical potentials on the target organ.

Figure 22:
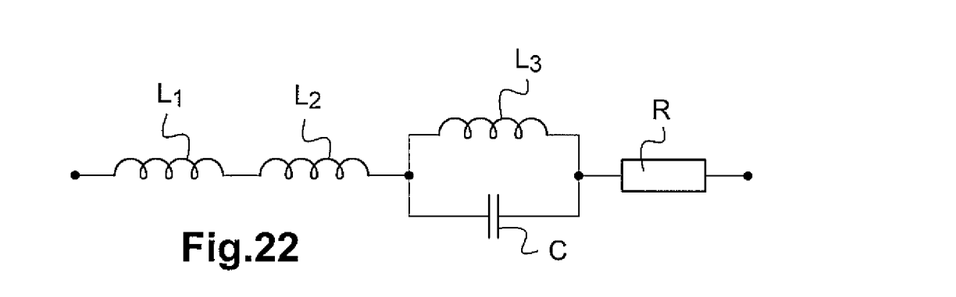
FIG. 22 illustrates an exemplary protective filter against the effects of RF fields of an MRI imager, made from components of the invention.

FIG. 22 illustrates a stop filter for protection against RF fields of an MRI imager.

This filter combines passive components produced in the method just described with reference to FIGS. 15 to 20. It comprises, for example, in series, two series inductors L1, L2, a L3+C3 plug circuit and a series resistor A.

Such an MRI filter may be incorporated at the lead termination so as to be located as close as possible of the electrodes or even in contact with the tissues in order to limit the heating and potentials induced by the electromagnetic field of the imager. The lead body no longer acts as an antenna (capture of the electromagnetic field), thus avoiding any risk of damaging the implantable generator as well as lesions of the stimulated tissues.

In general, whatever the passive component produced by the technique just described, it will be noted that the incorporation of this component by a simple weaving, embroidering, braiding or knitting technique makes it possible to retain the properties of deformability and extensibility of the interface with the target organ, which are mandatory properties in a neurostimulation application, as explained above.

Finally, it will be noted that the realization of the various patterns making it possible to obtain the passive component functions by weaving, embroidering, etc., is very easy to adjust and modify, by simple parameterization of the automated numerical control machine performing these weaving, embroidering, etc., functions.

The invention claimed is:

1. An implantable lead for electrically stimulating an organ and/or collecting electrical potentials thereon, comprising:
   a distal termination capable of coming into contact with the tissues of the organ, said termination comprising:
      an insulating substrate; and
      at least one conductive interface carried by the substrate; and
   a tubular lead body, comprising at least one bonding conductor extending therethrough and connected to the at least one conductive interface,
   the at least one conductive interface comprises at least one deformable conductive wire;
   the at least one conductive interface comprises a woven, embroidered, braided or knitted configuration for anchoring the at least one deformable conductive wire to the substrate; and
   said woven, embroidered, braided or knitted configuration comprises a pattern imparting to said at least one deformable conductive wire a passive component electrical function in a region of the pattern, the passive component electrical function comprising at least one of a capacitive function in the region of the pattern or an inductive function in the region of the pattern, the inductive function formed by winding the at least one deformable conductive wire on both sides of a plane of the substrate in the region of the pattern.

2. The lead of claim 1, wherein the substrate is a non-elastically deformable substrate and the at least one conductive interface is devoid of an additional elastically deformable support incorporating the substrate or adjoining the substrate.

3. The lead of claim 1, wherein the passive component electrical function further comprises a resistive function, the pattern comprising a zigzag pattern of the at least one deformable conductive wire on the substrate.

4. The lead of claim 1, wherein the passive component electrical function further comprises a resistive function, at least a portion of the at least one deformable conductive wire being in the region of the pattern an intrinsically resistive portion.

5. The lead of claim 1, wherein the capacitive function is formed by the at least one deformable conductive wire being interrupted in the region of the pattern and being configured on the substrate to form two non-electrically connected interleaved portions extending together leaving a coupling gap forming a capacitor dielectric therebetween.

6. The lead of claim 1, wherein the passive component electrical function further comprises an antenna function, the at least one deformable conductive wire comprising in the region of the pattern a free distal end configured on the substrate to form a radiofrequency radiating element.

7. The lead of claim 1, further comprising at least one wire of non-electrically connected ferromagnetic material, extending in the region of the pattern within the wound portion of the at least one deformable conductive wire and forming a core for the inductive function.

8. The lead of claim 1, the passive component electrical function further comprising one or more of the inductive function, the capacitive function, and a resistive function to form a stop filter tuned to at least one RF frequency of an MRI imager.

\* \* \* \* \*